US008343168B2

(12) United States Patent
Kaye et al.

(10) Patent No.: US 8,343,168 B2
(45) Date of Patent: Jan. 1, 2013

(54) ENDOSCOPIC DEVICE (75) Inventors: Christopher J. Kaye, Concord, OH (US); K. Randall John, Chardon, OH (US); Alexis Uspenski, Rock Creek, OH (US)

(73) Assignee: US Endoscopy Group, Inc., Mentor, OH (US)

( * ) Notice: Subject to any disclaimer, the term of this patent is extended or adjusted under 35 U.S.C. 154(b) by 433 days.

(21) Appl. No.: 12/021,903

(22) Filed: Jan. 29, 2008

(65) Prior Publication Data
US 2008/0183184 A1    Jul. 31, 2008

Related U.S. Application Data (60) Provisional application No. 60/898,089, filed on Jan. 29, 2007.

(51) Int. Cl.
*A61B 17/24*    (2006.01)
*A61B 17/26*    (2006.01)

(52) U.S. Cl. ........................................ 606/110; 600/104
(58) Field of Classification Search .......... 606/110–115, 606/172; 600/104
See application file for complete search history.

(56) References Cited

U.S. PATENT DOCUMENTS

| | | | |
|---|---|---|---|
| 4,966,589 A | 10/1990 | Kaufman | |
| 5,009,642 A * | 4/1991 | Sahi | 604/158 |
| 5,964,740 A | 10/1999 | Ouchi | |
| 5,997,547 A | 12/1999 | Nakao et al. | |
| 6,093,195 A | 7/2000 | Ouchi | |
| 6,669,716 B1 * | 12/2003 | Gilson et al. | 623/1.11 |
| 6,827,710 B1 | 12/2004 | Mooney et al. | |
| 6,945,956 B2 | 9/2005 | Waldhauser et al. | |
| 7,001,354 B2 | 2/2006 | Suzuki et al. | |
| 2005/0107668 A1 | 5/2005 | Smith | |
| 2005/0267490 A1 | 12/2005 | Secrest et al. | |

FOREIGN PATENT DOCUMENTS

JP    3-54652    5/1991

OTHER PUBLICATIONS

Office Action from U.S. Appl. No. 11/137,814, dated Feb. 12, 2009.
International Search Report and Written Opinion from International Application No. PCT/US08/052342, mailed Jul. 30, 2008.
JP 2009-584397 Office Action mailed Sep. 28, 2012, including an English Translation.

* cited by examiner

*Primary Examiner* — Kathleen Holwerda
*Assistant Examiner* — Katherine M Shi
(74) *Attorney, Agent, or Firm* — Calfee, Halter & Griswold, LLP (57) ABSTRACT A medical device having a member with a lumen extending from a proximal end to a distal end of the member is disclosed. The lumen has a device portion defined by at least one curved walled portion and at least one anchoring portion. An endoscopic device, such as a needle, is attached to an actuator inserted into the device portion of the lumen. A housing or stop is inserted into the distal end of the lumen.

17 Claims, 8 Drawing Sheets

ENDOSCOPIC DEVICE

CROSS-REFERENCE TO RELATED APPLICATIONS

This non-provisional application claims the benefit of U.S. Provisional Patent Application No. 60/898,089, entitled "Snare Injection Device," filed Jan. 29, 2007, which is hereby incorporated in its entirety, to the extent that it is not conflicting with the present application.

FIELD OF THE INVENTION

The invention relates to a medical device for performing endoscopic procedures and to an endoscopic device having a needle.

BACKGROUND OF THE INVENTION

Endoscopes are well-known in the art and are commonly used for numerous medical procedures. One exemplary procedure is removing polyps, lesions or other types of targeted tissue from the gastrointestinal mucosal wall of a human subject. Various cauterization devices have been developed to remove polyps. These devices, however, sometimes cause serious thermal injury to the gastrointestinal wall, fail to remove the entire targeted tissue, or do not completely cauterize blood vessels which lead to excessive bleeding. Snare devices designed to encircle and remove polyps often do not capture all of the targeted tissue. Further, a physician may experience difficulty in securing the targeted tissue with the snare. Snaring only the minimal tissue required from the three layer wall, i.e., mucosa, submucosa, and muscularis, is also important. More specifically, to prevent complications, the muscularis tissue should be avoided all together in this type of procedure. In an effort to solve these and other problems, one technique used is a sub-mucosal lift polypectomy, which involves using a needle to inject the tissue with, for example, a saline solution, to lift the tissue to a more favorable position. This technique improves complete transection. The injected fluid separation also insulates the outer muscle from cautery or thermal injury.

Various other endoscopic procedures require a needle, including use of a needle for: washing a targeted work site; applying dies for the purpose of highlighting diseased or abnormal tissue; injecting tattoo medium for post-transection surveillance purposes; and hemostatic injection therapy for post-polypectomy bleeding. In these and other procedures requiring a needle and a second endoscopic device, a physician must use two separate auxiliary instruments, and one at a time feed the devices in and out of the instrument channel of an endoscope, which increases the overall procedure time.

In certain situations, the needle may be combined with a second endoscopic device in one auxiliary instrument having a multiple lumen catheter. However, combining a needle with a second endoscopic device in a multiple lumen catheter can be problematic. For example, the needle may puncture the multiple lumen catheter or deploy beyond a desired length, injuring the patient. Further, radio frequency energy used to energize the second endoscopic device, for example a cauterization snare, may be transferred to other portions of the device, which in turn would direct the current away from the targeted tissue. Also, the incorporation of a needle stop to prevent the needle from falling out of the catheter may result in "lost motion." If the needle lumen is made large enough to allow the addition of the needle stop, the actuator that is attached to the needle and the needle itself will fit very loosely within the needle lumen, and be free to move within the needle lumen. This type of freedom of movement is referred to as "lost motion" in the art.

SUMMARY OF THE INVENTION

The invention offers numerous advantageous features including a needle limit mechanism, consistent 1:1 handle/needle axial movement in a variety of endoscope configurations to prevent "lost motion," and puncture prevention features. Further, the medical device includes non-conductive portions that prevent radio frequency energy used to energize the snare from transferring to other portions of the device, which in turn would direct the current away from the targeted tissue.

In one exemplary embodiment of the invention, the medical device includes a member having a lumen extending from a proximal end to a distal end of the member. The lumen has a device portion defined by at least one curved walled portion and at least one anchoring portion. An endoscopic device, such as a needle, is attached to an actuator inserted into the device portion of the lumen. A housing or stop is inserted into the distal end of the lumen. The housing permits deployment of the needle, prevents puncture of the lumen, and prevents "lost motion."

BRIEF DESCRIPTION OF THE DRAWINGS

Further features and advantages of this invention will become apparent from the following detailed description made with reference to the accompanying drawings.

DETAILED DESCRIPTION OF THE INVENTION

This Detailed Description of the Invention merely describes embodiments of the invention and is not intended to limit the scope of the specification in any way. Indeed, the invention as described by the specification is broader than and unlimited by the preferred embodiments, and the terms used in the specification have their full ordinary meaning.

A medical device having a needle for performing endoscopic procedures is disclosed. The needle device is described for use with a snare in a snare injection device. However, it should be understood that this is for exemplary purposes only and the needle device may be used alone or with a variety of endoscopic devices. Further, the invention will be described for use with an endoscope having an instrument channel. It should also be understood that this is for exemplary purposes only and the invention can be applied to a wide variety of applications.

In embodiments of the invention having a dual lumen member, the needle and second endoscopic device are generally individually routed within separate lumens of a dual lumen member. However, in certain embodiments, the needle may be routed within a single lumen of a single lumen member. The needle and the second endoscopic device are independently deployable by manipulation of separate control handles by one or two medical operators. In discussing the device, the terms distal and proximal are used with respect to the operator's hand. In other words, when the device is used within the auxiliary channel of an endoscope or similar device, the proximal and distal orientation are relative to the surgeon or operator of the device, and not the internal work site within the patient.

In an exemplary embodiment, the device includes a needle and a second endoscopic device, each separately routed in one lumen of a dual lumen member. The needle may perform several functions during the procedure, including pre-procedure and postprocedure injections, and lifting the tissue during the procedure. The device also allows for immediate repeat injections which may be required due to absorption of the lift fluid by the gastrointestinal wall, without removal of the second endoscopic device.

The invention offers numerous other improvements over prior art needle devices including a needle limit mechanism, consistent 1:1 handle/needle axial movement in a variety of endoscope configurations to prevent lost motion, and puncture prevention features. In certain prior art designs, a needle could injure a patient by puncturing the sidewall of a device or deploying beyond a desired length to cause harm to a patient. As such, the present invention offers improvements in patient safety and ease of use for the physician.

Figure 1:
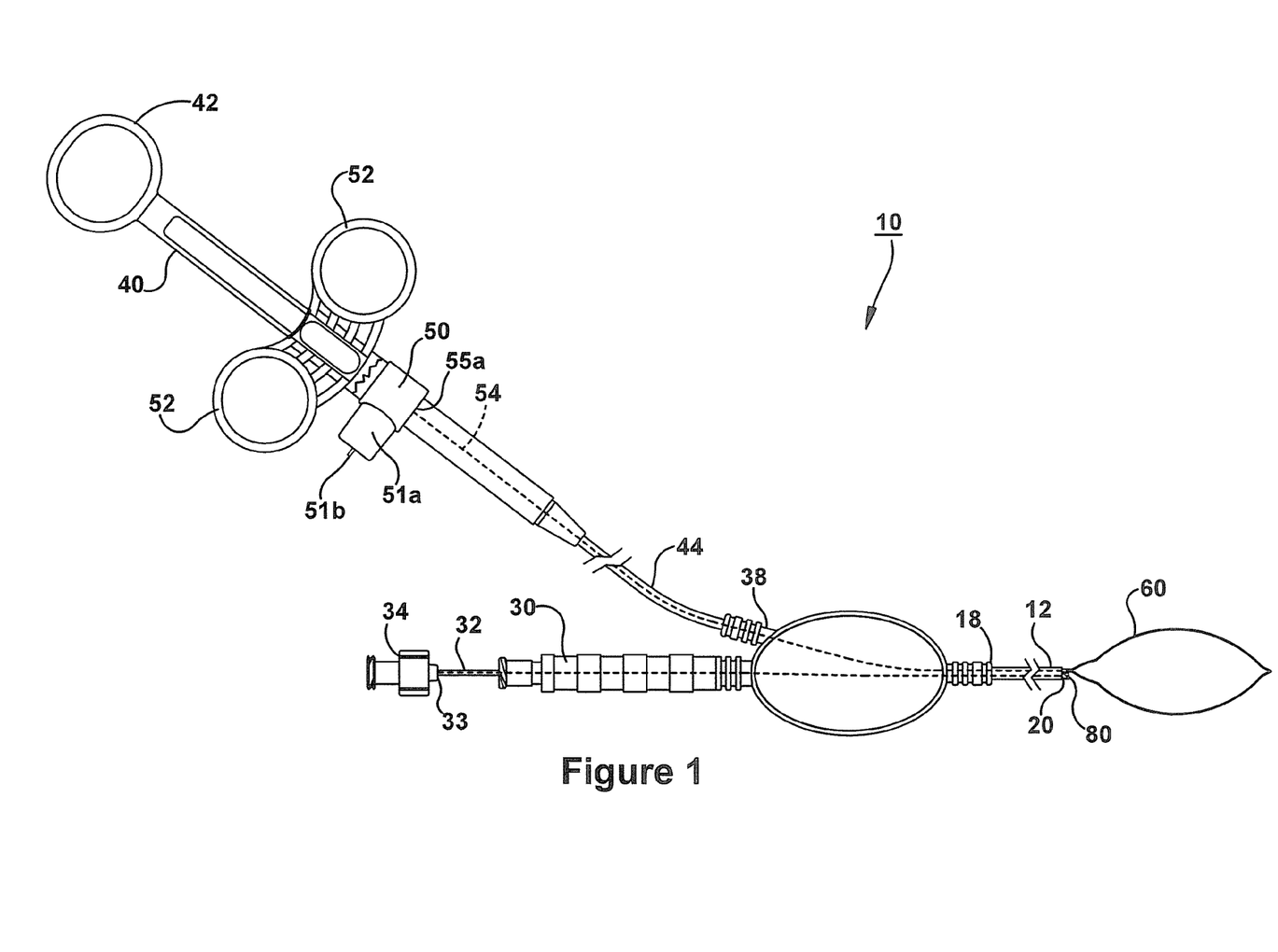
FIG. 1 is a side view of a device according to an embodiment of the invention, wherein the device has a snare (shown deployed) and a needle.
Figure 2:
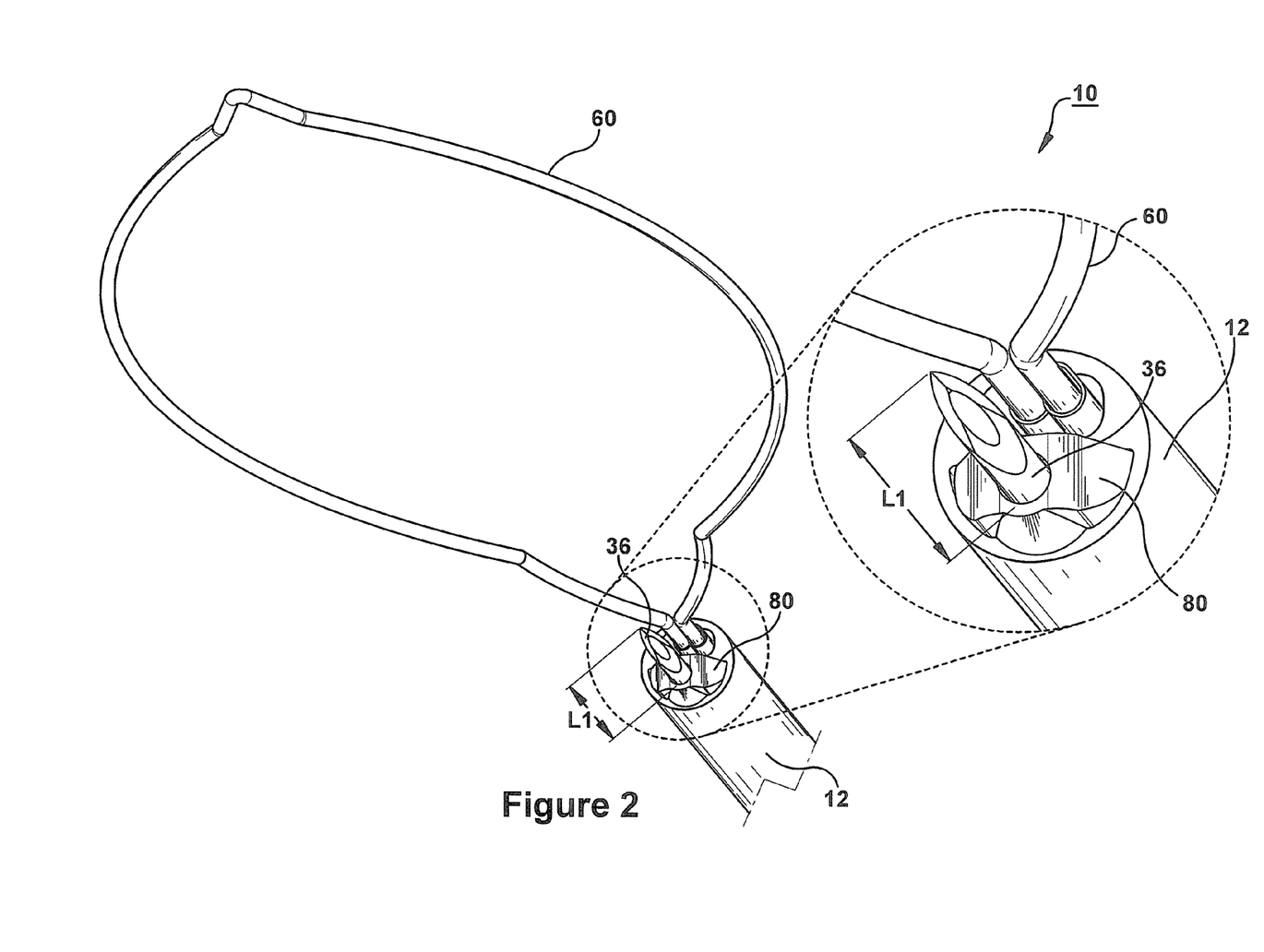
FIG. 2 is an enlarged perspective view of the distal end of the device of FIG. 1, showing the snare and the needle deployed.

Referring now to the drawings, a snare injection device 10 for use with an endoscope is illustrated in FIG. 1. The device is suitable for use in polypectomy procedures and any other procedure in which injection and snare capability is required. In FIG. 1, the snare 60 is shown in an expanded position. As shown, the device 10 utilizes an oval snare. However, it should be apparent to those skilled in the art that various sizes and shapes of snares may be utilized effectively, for example a hexagonal snare or some other polygonal shape. FIG. 2 is an enlarged perspective view of the distal end of the device 10, showing the snare 60 expanded and the needle 36 deployed. The device allows a physician to perform either technique, i.e., operation of the snare 60 or the needle 36, without removing the device 10 from the instrument channel. An exemplary snare and needle device is disclosed in U.S. patent application Ser. No. 11/137,814, entitled "Snare Injection Device," filed May 25, 2005, and is hereby incorporated in its entirety, to the extent that it is not conflicting with the present application.

As shown in FIG. 2, the device 10 includes an elongated member 12, or catheter. The depicted member 12 has two lumens or channels, a first lumen (i.e., a needle lumen) and a second lumen (i.e., a snare lumen), each lumen leading from a proximal end 18 to a distal end 20 of the member 12. As stated, in certain embodiments, the member may have only a single lumen or channel. The member 12 shown is a single piece of extruded plastic and may be constructed from a variety of flexible materials, such as for example but not limited to, polytetrafluorethylene (PTFE) or polyethylene tubing. Various first and second lumen sizes and shapes may be used in the practice of the invention, as will be discussed. Further, it should be apparent to one with ordinary skill in the art that the member of the invention may be practiced with a single piece of extruded dual lumen tubing, or alternatively, with a dual lumen assembly including separate tubing and a sheath or other suitable covering. The distance $L_1$ the needle protrudes is pre-determined by a needle housing (discussed more fully below) and a spring housed in the base 30 of the device 10. The distance $L_1$ is determined by performance and safety criteria, and can vary in the practice of the invention.

Figure 3:
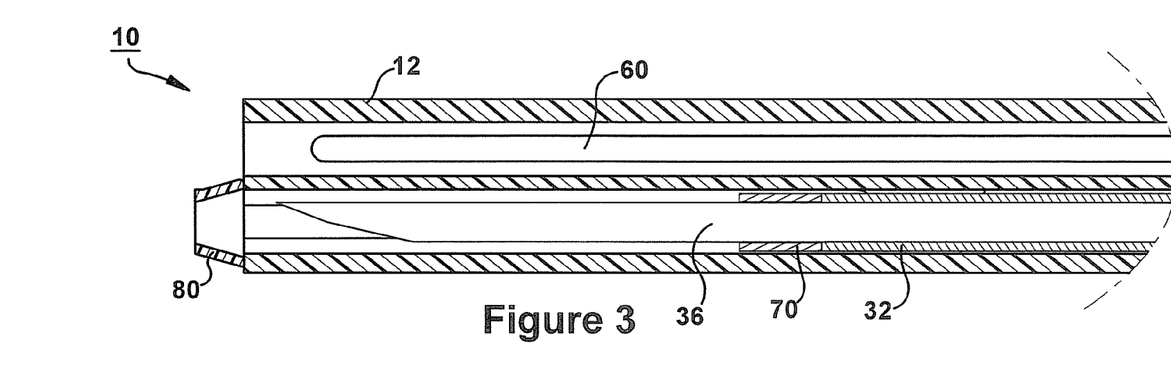
FIG. 3 is a cross sectional view of a distal end of the device of FIG. 1, showing the needle retracted.

A fluid delivery system for use to inject tissue within the body may be part of the device 10. The delivery system generally includes a hollow base 30 fixed to a proximal end 18 of the member 12. The base 30 provides support for an actuator tube 32 that is threaded through the base and can be moved relative thereto. The actuator tube 32 has a proximal end 33 and a distal end. As shown, the tube 32 is inserted through the base 30 and the first lumen. The actuator tube 32 can be manipulated by movement of a hollow knob 34. The knob 34 is fixed to the actuator tube 32 proximal end 33. The needle 36 is fixed to the actuator tube 32 distal end. In this position, a fluid solution can be passed under pressure through the knob 34 to the needle 36. To deploy the needle 36, the operator presses the knob 34 toward the base 30. When the knob 34 is released, a spring mechanism (not shown) disposed internally in the base 30 forces the knob 34 and needle 36 to return to their at rest position (as shown in FIG. 3). It should be noted that the invention may also be used in systems without a fluid delivery system. In these systems, the needle may be attached to an actuator, such as a cable.

The base 30 further includes a side entry port 38. As shown, this port 38 is angled less than 45 degrees with respect to a longitudinal axis of the base 30. It is believed this angled structure reduces binding within the dual lumen member 12. The resulting y-shaped base may be a single molded piece or a multiple part assembled piece.

A snare system for transecting tissue is included in the device 10. The snare system can be used to remove tissue, such as for example, a polyp after it has been lifted by the injection of a fluid. The snare 60 is shown in a collapsed or retracted position in FIGS. 3 and 4. The system includes an elongated body 40 having a thumb ring 42 at a proximal end. A handle 50 is formed on the body 40 as a separate piece. The handle is slidable relative to the body in either a distal or proximal direction by manipulation of two finger rings 52. The base 40 and handle 50 are formed of a rigid plastic material, although any suitable material may be used in the practice of the invention. The snare system includes a cable 54, or actuator, that extends substantially through the second lumen of the member 12. The cable 54 has a proximal end 55a fixed to the handle 42 and a distal end fixed to a connector connecting the cable to the snare 60. As shown, the cable 50 further passes through a flexible tube 44 that remotely connects the body 40 to the inlet port 38. The tube 44 may be constructed from any flexible, durable material such as polyethylene or PTFE. However, this junction may also be constructed from a rigid material.

Figure 4:
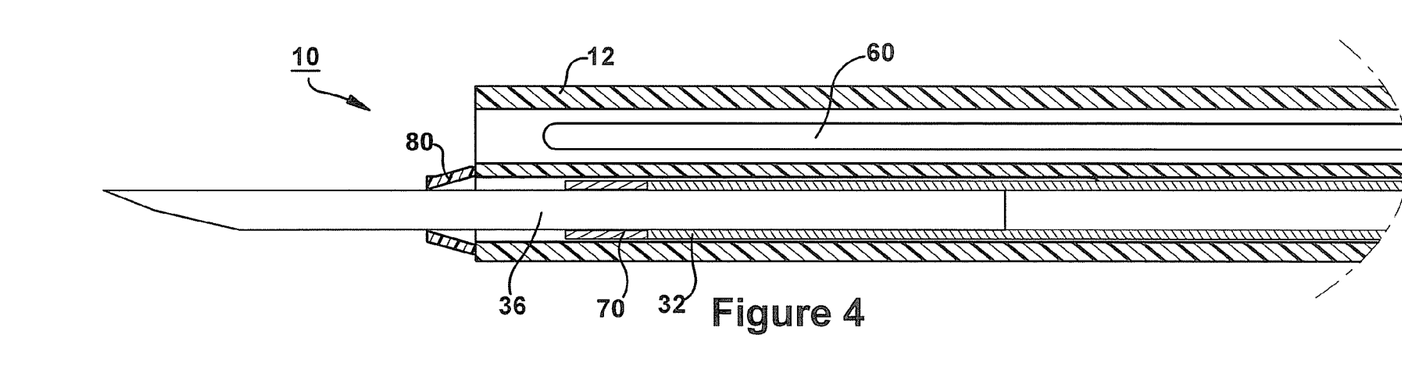
FIG. 4 is a cross sectional view of the distal end of the device of FIG. 1, showing the needle at least partially deployed.

In FIGS. 3 and 4, a range of motion of the needle 36 of the device 10 is illustrated. FIG. 3 is a cross sectional view of the needle 36 retracted in a stored position within the first lumen of the member 12. In this position, no axial forces are on the needle 36. FIG. 4 is a cross sectional view of the needle 36 in a partially deployed position. As shown, a hub 70 on the needle 36 is sized to prevent the needle from deploying beyond a desired distance or falling out of the first lumen. The needle 36 may be attached to the actuator tube 32 by any suitable method known in the art. For example, the needle 36 may be press fit in the distal end of the actuator tube 32 or attached to the actuator tube by a connector. Further, the hub 70 and the needle 36 may be made of a unitary construction.

As shown in FIGS. 3 and 4, the needle 36 is disposed within a needle housing member 80 (i.e., a needle stop or guide) attached to the first lumen. The housing member 80 provides a guide for the needle assembly (preventing "lost motion"), limits the travel of the needle, and prevents the needle from puncturing the lumen or falling out of the catheter. The housing member 80 may be disposed in place by being heat shrunk, press fit, bonded, or other suitable known method. The housing member 80 may also have barbs, or ribbed sections, that create a friction surface against the first lumen to hold the housing member in place. The housing member 80 may be constructed from any coated metal or non-conductive suitable material, such as for example, a medium hardness plastic. A benefit of the housing member 80 being non-conductive is radio frequency energy used to energize the snare 60 does not transfer to the housing member which in turn would direct the current away from the targeted tissue. The housing member 80 may include two or more pieces joined together. The housing member is discussed in greater detail below.

Figure 5:
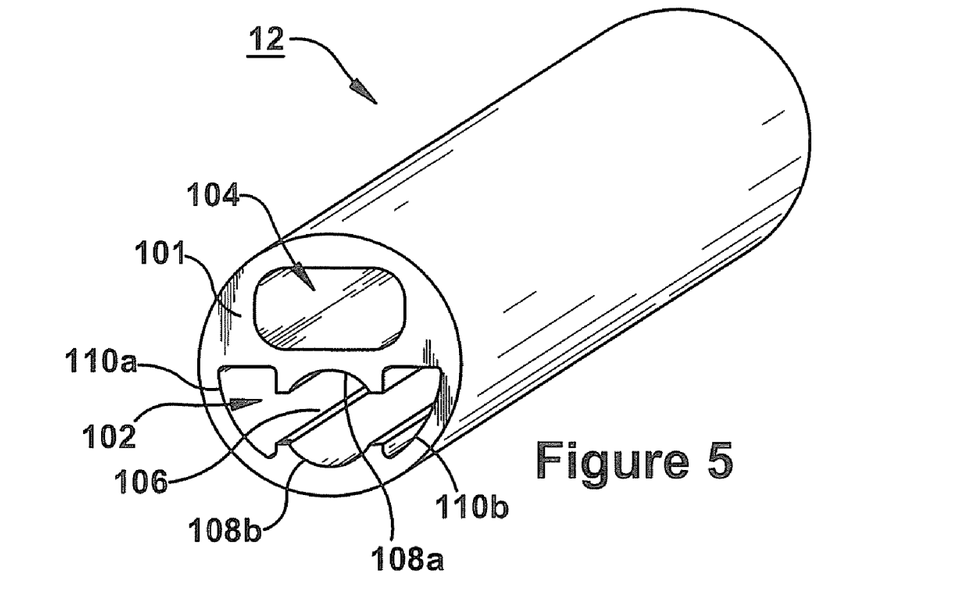
FIG. 5 is a perspective view of a member of the device of FIG. 1, wherein the member has two lumens.
Figure 6:
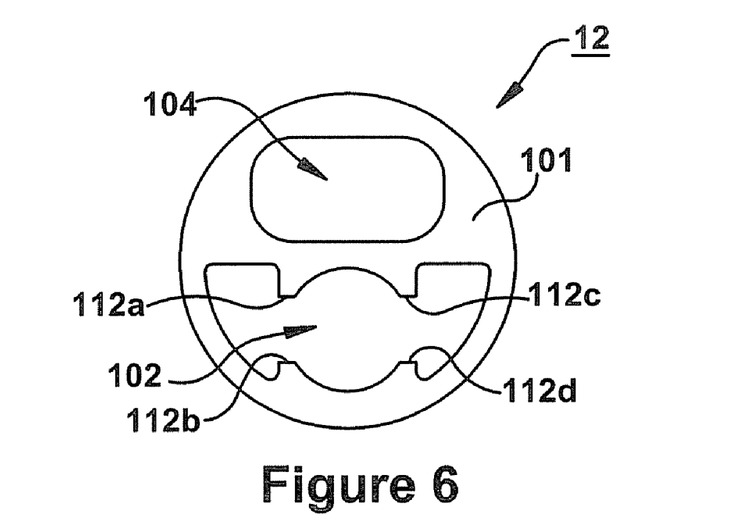
FIG. 6 is a cross sectional view of the member of FIG. 5.

FIG. 5 shows a front perspective view of the member 12, or catheter. As stated, the member 12 has two lumens, i.e., it is a dual lumen member or catheter. However, in certain embodiments, the member may have more or less lumens, for example a single needle lumen. The member 12 includes a front face 101, a needle assembly or needle lumen 102 and a snare assembly or snare lumen 104. A cross sectional view of the dual lumen member 12 is shown in FIG. 6.

The needle lumen 102 is formed from three connecting portions, a device or center portion 106 and two anchoring or outer wing-shaped portions 110a, 110b. The center portion 106 is formed by two curved walled sections 108a, 108b. As illustrated, the center portion 106 formed by the two curved walled sections 108a, 108b is circular in shape along its longitudinal length. To be discussed further in greater detail, the center portion 106 houses a needle assembly. The outer portions 110a, 110b of the needle lumen are disposed at either side of the center portion 106. As best seen in FIG. 6, four elongated ridges 112a, 112b, 112c, 112d define narrowed connections between the center portion 106 and the outer portions 110a, 110b.

The multiple lumen member 12 geometry improves the device performance and allows the incorporation of components that would otherwise be very difficult or impossible. The needle lumen 102 addresses certain challenges. Specifically, one challenge is the incorporation of the needle housing 80 (i.e., a needle stop or guide) at the distal end of the needle lumen 102. If the needle lumen 102 is made large enough to allow the addition of the needle housing 80, the actuator tubing 32 that is attached to the needle 36 and the needle itself will fit very loosely within the needle lumen, and be free to move within the needle lumen. This type of freedom of movement is referred to as "lost motion" in the art. In other words, additional, undesired axial needle motion must be accounted for due to the length of a typical device, e.g., up to 230 cm. The situation is exaggerated as the path of the device through the body becomes more difficult and complex, sometimes due to unfavorable internal conditions. Specifically, the difficulty is due to the preferred path of the actuator tube 32 with respect to needle lumen 102.

Figure 8A:
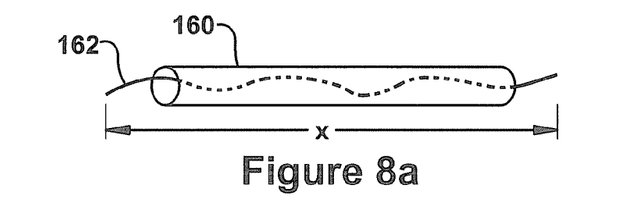
FIGS. 8a-8b are schematics showing the concept of lost motion.
Figure 8B:
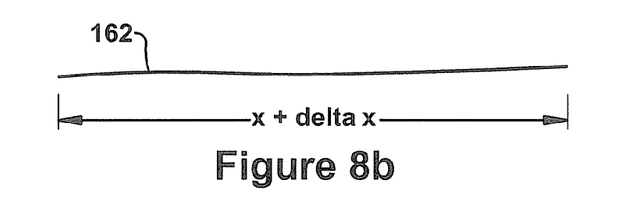

To clarify the concept of lost motion, consider the known D-shaped catheter lumen. Generally, the round needle actuator tubing fits rather loosely in this channel, allowing motion in a side-to-side or radial direction. This side-to-side motion may be slight over a short length, but the additive effects over the 90 plus inches of the device must be accounted for or the needle will not extend out to its intended length. An example of lost motion is illustrated in FIGS. 8a-8b. A needle actuator tube 162 is shown in FIG. 8a within a catheter 160. The tube 162 travels a distance x. FIG. 8b illustrates the actual length of the actuator tube is x plus delta x. The length of delta x is the lost motion of the needle actuator tube.

Because it is also essential that the needle fully retract, the spring design (with respect to energy and free-length) must address the additional potential travel. In contrast, utilizing the lumen shape shown in FIGS. 5-6 (or other geometry shapes of this invention) provides control of the actuator tubing so that the lost motion is significantly limited. Reducing lost motion allows the overall compensation length to be reduced so that the full axial travel of the actuator tubing and needle (that is influenced by the spring) is less, making the operation more efficient.

With the invention, the center lumen portion 106 is sized to the needle 36 and actuator tubing 32 only, thereby reducing the amount of lost motion. The outer portions 110a, 110b of the needle lumen 102 are available for other functions, such as for example but not limited to, the locking portion, such as the legs, of the needle housing 80. The connecting openings defined by the elongated ridges 112a, 112b, 112c, 112d improve the manufacturability of the catheter lumen and also reduce the friction that occurs between the actuator tube 32 and the dual lumen member 12, due to less surface area for these items to contact.

The snare lumen 104 defines an elongated passage for housing the snare assembly. The capsule shaped lumen 104 improves the performance of the snare by allowing adequate space for the snare loop wires to reside and at the same time creating alignment for the snare with respect to the snare lumen. In the practice of the invention, other endoscopic instruments could be installed within the second lumen 104.

Figure 7A:
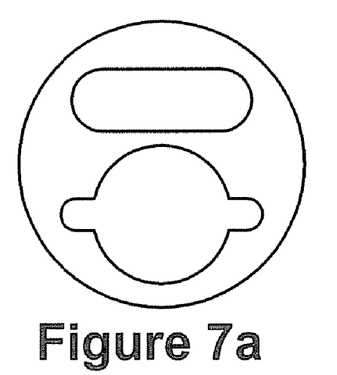
FIGS. 7a-7e are cross sectional views of various exemplary members made in accordance with the invention.
Figure 7B:
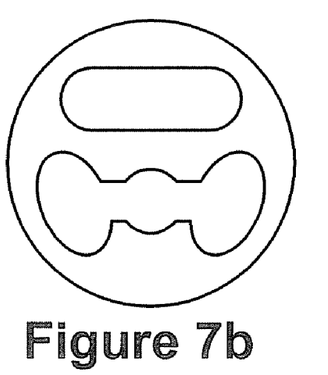
Figure 7C:
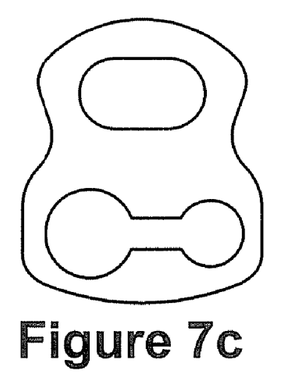
Figure 7D:
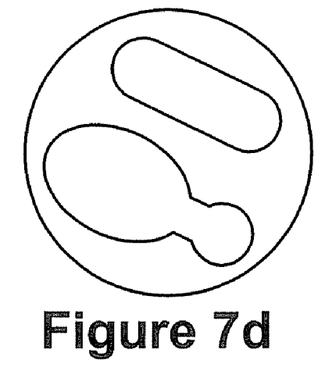
Figure 7E:
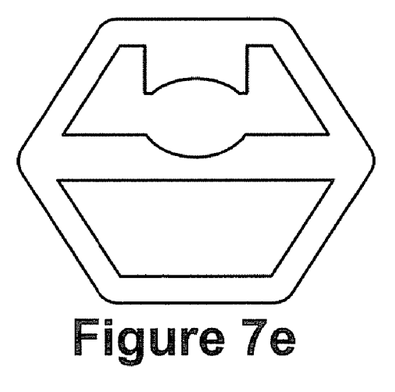

It should be understood by others with ordinary skill in the art that the geometry of the dual lumen member 12 illustrated in FIGS. 5 and 6 is exemplary only. The shape, size and configuration of either lumen may vary in the practice of the invention, such as for example but not limited to, the dual lumen member designs illustrated in FIGS. 7a-7e. Further, the outer surface of the member may be a variety of shapes, sizes, and configurations, such as the shape and configuration shown in FIG. 7c.

Referring now to FIGS. 9-13, various views of the needle housing 80 (i.e., a needle stop or guide) are shown. The needle housing 80 includes a base 122 and two legs 124, 126. The base 122 has a relatively flat front surface 128 and two opposing outer surfaces 160, 162 that are angled back toward the proximal end of the two legs 124, 126.

The legs 124, 126 are correspondingly sized to engage each outer portion 110a, 110b of the dual lumen member 12. In an installed position within the dual lumen member 12, the legs 124, 126 anchor the needle housing 80 in place. The needle housing 80 may be one integral piece or formed from multiple pieces. The needle housing 80 may also be flexible. Further, the needle housing 80 may be injection molded to minimize cost, and can be constructed of a non-conductive material. It should be noted that a coated metal part, such as for example, machined or metal-injection-molded, or a ceramic part could also achieve the same non-conductive effect. Keeping this component non-conductive ensures that no electrical arcing occurs between the snare (which is energized during cautery) and the needle housing. The risk of exposure to collateral patient tissue is lowered by reducing the likelihood of arcing.

Figure 10:
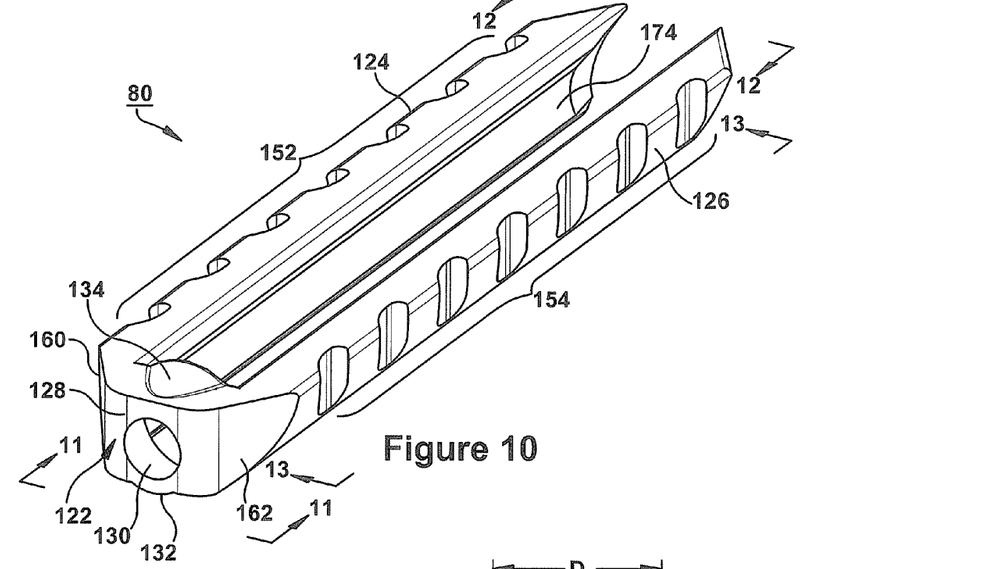
FIG. 10 is front perspective view of the needle housing of FIG. 9.
Figure 11:
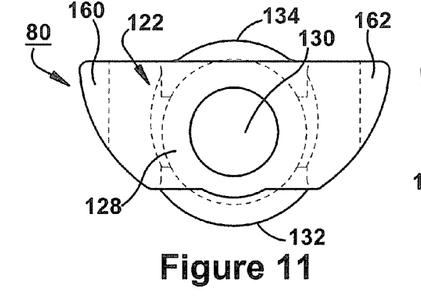
FIG. 11 is a front view of the needle housing of FIG. 9.
Figure 12:
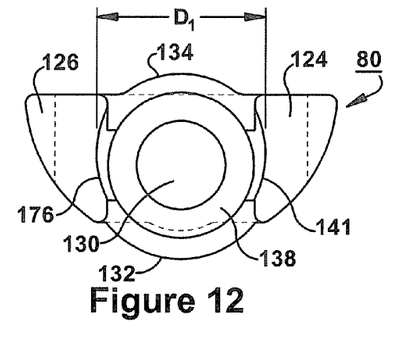
FIG. 12 is a rear view of the needle housing of FIG. 9.
Figure 13:
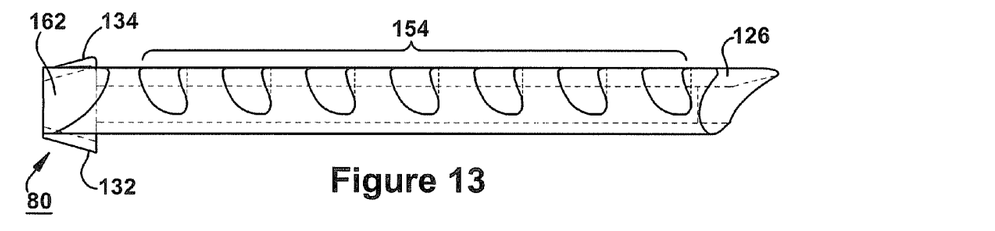
FIG. 13 is a side view of the needle housing of FIG. 9.

FIG. 10 is a front perspective view of the needle housing 80. A front face 128 of the base 122 defines a through hole 130. As shown in FIG. 2, the through hole 130 is sized to permit the deployment of the needle 36. A bottom edge and a top edge of the front face are useful for orientation and are defined by curved edge surfaces 132, 134.

Figure 9:
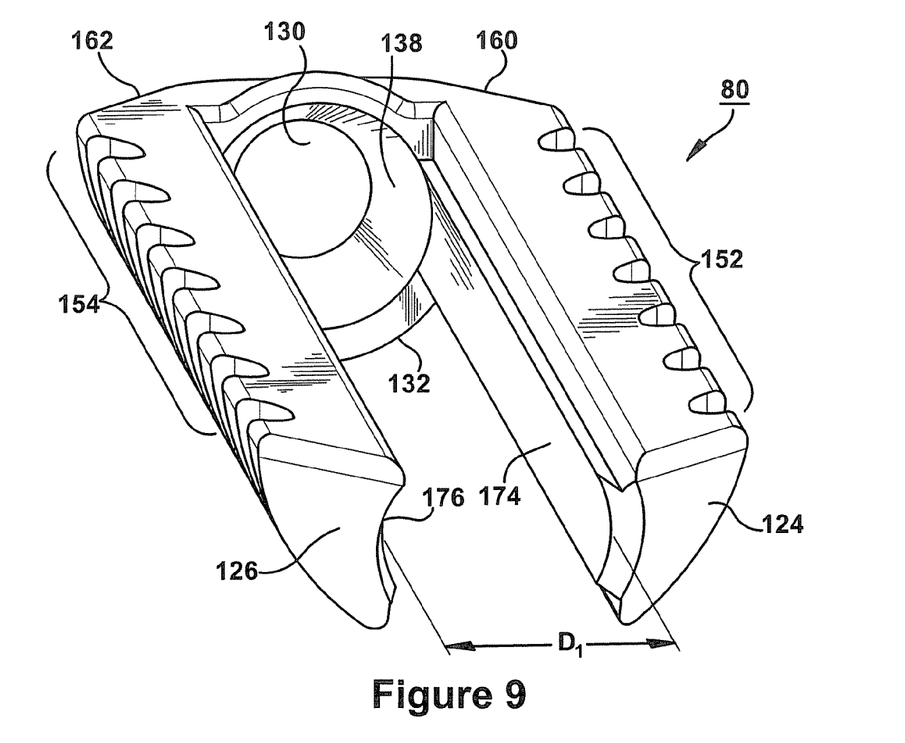
FIG. 9 is a rear perspective view of a needle housing of the device of FIG. 1.

A rear perspective view of the needle housing 80 is illustrated in FIG. 9. The legs 124, 126 contain a ribbed section 152, 154, respectively. In an installed position within the outer portion 110a, 110b, each ribbed section 152, 154, respectively, creates a press-fit friction surface that holds the housing 80 in place. It should be understood that various rib patterns, sizes and shapes can be used in the practice of the invention. Further, adhesive or other permanent mounting techniques may be used in the practice of the invention to fix the housing 80 within the dual lumen member 12.

The center base 122 of the housing 80 provides a needle guide and needle stop that are important features of the invention. The legs 124, 126 guide the travel path of the needle 36 and needle actuator or actuator tube 32 within the dual lumen member 12. The inner surface 176 of the leg 126 and the inner surface 174 of the leg 124 form a partial-walled cylinder. Consequently, the needle 36 cannot puncture the sidewalls of the needle lumen 106 in a stored position. An entry port to the cylinder at the proximal end has a diameter $D_1$. The cylinder has a smaller diameter along its length until the conical concave surface 138. As the needle 36 deploys from a retracted position out the through hole 130, the conical surface 138 may stop axial movement of the needle in the distal direction by prohibiting movement of the optional fitting or connector 70 or a hub on the needle (i.e., a portion of the needle assembly with a larger outer diameter than the diameter of the hole). A portion of the needle with an outer diameter larger than the diameter of the hole 130 prevents the needle 36 from falling out of the catheter and into the patient if the needle comes loose from the actuator or actuator tube 32. The conical surface 138 of the housing 80 also assists in aligning the needle 36 with the hole 130 as the needle is deployed.

Figure 14:
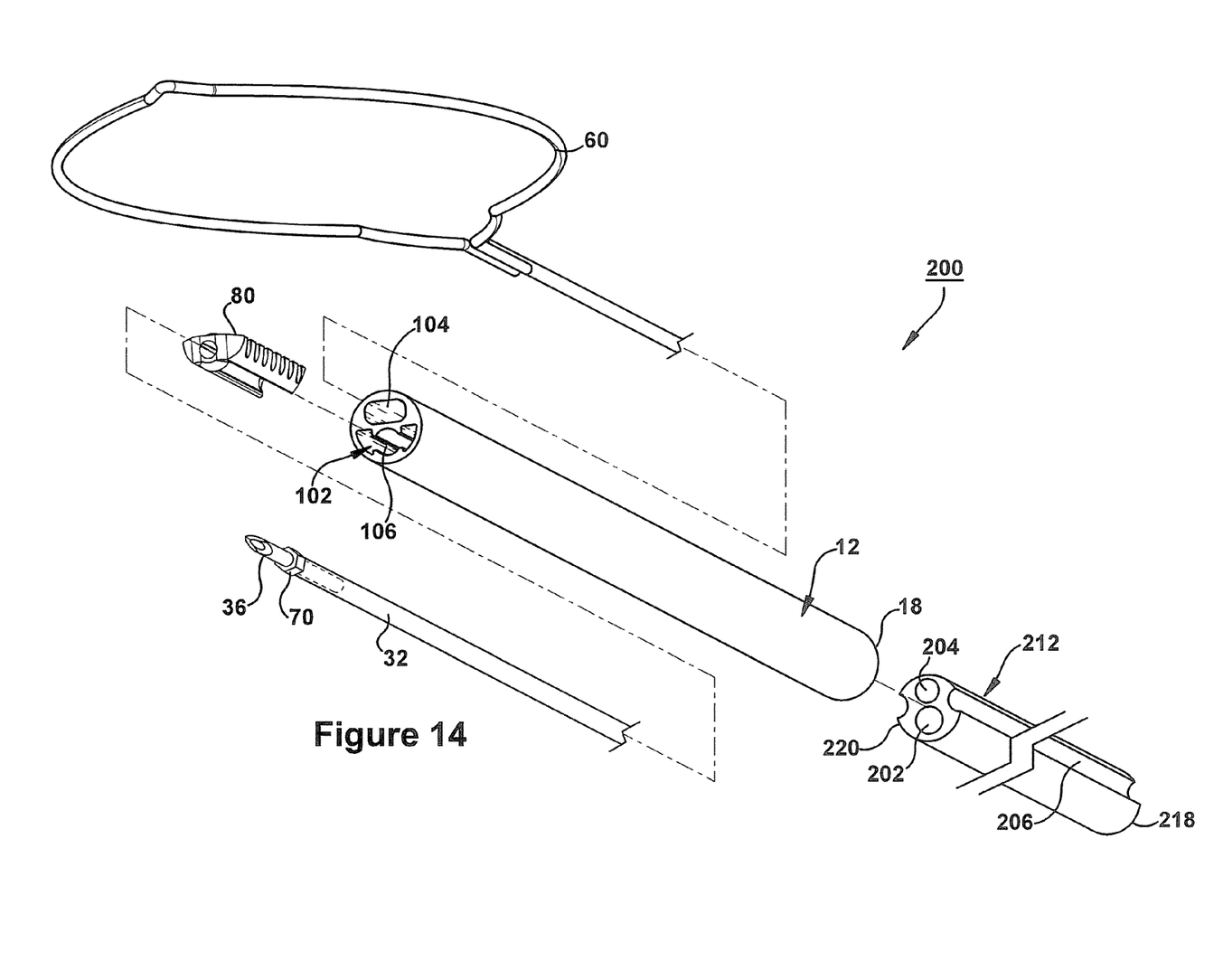
FIG. 14 is an assembly view of a device according to another embodiment of the invention, wherein the device has a snare, a needle, a needle housing, and two members, each member having two lumens.

Referring now to FIG. 14, an assembly view of a device 200 is illustrated. The device 200 is similar to the device 10 shown in FIG. 1. Similar to device 10, device 200 includes a snare 60; a needle housing 80; a first dual lumen member 12 having a needle lumen 102 and a snare lumen 104; and a needle assembly having a needle 36, a connector or hub 70, and an actuator tube 32. However, the first dual lumen member 12 is connected to a second dual lumen member 212 in the depicted device 200. The second member 212 has a first or needle actuator lumen 202 and a second or snare actuator lumen 204, each lumen 202, 204 leading from a proximal end 218 to a distal end 220 of the second member 212. In certain embodiments, however, the second member 212 may have only a single lumen or channel. The distal end 220 of the second member 212 is connected to the proximal end 18 of the first member 12 and the proximal end 218 of the second member is connected to a base (not shown) of the device 200, for example similar to the base 30 shown in FIG. 1.

The second member 212 shown in FIG. 14 is a single piece of extruded plastic and may be constructed from a variety of flexible materials, such as for example but not limited to, polytetrafluorethylene (PTFE) or polyethylene tubing. Various first 202 and second 204 lumen sizes and shapes may be used in the practice of the invention. The outer surface of the member 212 may also be a variety of shapes, sizes, and configurations, for example cylindrical with ridges or grooves 206, as shown in FIG. 14. Further, it should be apparent to one with ordinary skill in the art that the member 212 may be practiced with a single piece of extruded dual lumen tubing, or alternatively, with a dual lumen assembly including separate tubing and a sheath or other suitable covering.

The second member 212 may be connected to the first member 12 such that the first or needle actuator lumen 202 is substantially aligned with at least the center portion 106 of the needle lumen 102 and the second or snare actuator lumen 204 is substantially aligned with the snare lumen 104. Generally, the second member 212 includes the majority of the total length of the catheter. For example, in a catheter that is approximately 88 inches in total length, the second member 212 may be 85 inches starting from the proximal end of the catheter connected to the base of the device, and the first member 12 may be the remaining 3 inches at the distal end of the catheter.

When assembled, the needle assembly and the needle housing 80 reside in the needle lumen 102 of the first member 12 while only the actuator or actuator tube 32 resides in the needle actuator lumen 202 of the second member 212. Similarly, the snare assembly resides in the snare lumen 104 of the first member 12 while only the snare actuator resides in the snare actuator lumen 204 of the second member 212. One benefit of having a second member 212 is that the majority of the total catheter length may be manufactured from bulk or standard stock, decreasing the overall cost of the device. Further, the first member 12 may be interchanged with members having lumens capable of supporting other various endoscopic devices known in the art, such as for example, a net.

The second member 212 may be connected to the first member 12 by any suitable method known in the art, such as for example with a connector, heat shrink, an adhesive, or any combination thereof. A connector may attach to the outside or inside of the first or second member. For example, the connector may include barbs sized and shaped to fit in the outer winged portions of the first member (the legs of the needle housing generally do not occupy the entire length of the first member). Further, a connector may include a ring that fits around the outer surface of the catheter. The connector may be covered with heat shrink and be molded.

While several embodiments of the invention has been illustrated and described in considerable detail, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the specification filed herewith.

We claim:

1. A medical device for performing endoscopic procedures, comprising:
    a member having at least one lumen extending from a proximal end to a distal end, wherein the at least one lumen has both a device portion and at least one anchoring portion, wherein the device portion is defined by at least one curved walled portion, wherein the device portion and the at least one anchoring portion are disposed parallel along a length of the member, and the at least one curved walled portion defines at least a portion of a perimeter of the device portion from a center point thereof;

an actuator having a proximal end and a distal end disposed within the device portion of the at least one lumen;

an endoscopic device attached to the distal end of the actuator; and a housing having a base and at least one leg, wherein the at least one leg is fixed to the at least one anchoring portion of the at least one lumen, and the base has a hole sized to permit deployment of the endoscopic device therethrough;

wherein the at least one lumen is operably configured to reduce side-to-side motion of the actuator, and to reduce friction between the endoscopic device and the member, by:

i) having the at least one curved wall portion adjacent to the actuator from the proximal end to the distal end of the member; and ii) fixing the at least one leg to the at least one anchoring portion at a location outside of the perimeter of the device portion.

2. The medical device of claim 1 further comprising at least one connection between the device portion and the at least one anchoring portion.

3. The medical device of claim 2, wherein two elongated ridges define the at least one connection between the device portion and the at least one anchoring portion.

4. The medical device of claim 1, wherein the device portion is defined by two curved walled portions defining an inner diameter at least as large as an outer diameter of the actuator.

5. The medical device of claim 1, wherein the at least one leg is sized to engage the at least one anchoring portion of the at least one lumen to create a press fit when the at least one leg is inserted into a distal end of the at least one anchoring portion.

6. The medical device of claim 5, wherein the at least one leg further comprises at least one ribbed section that creates a friction surface against the at least one anchoring portion of the at least one lumen.

7. The medical device of claim 5, wherein an adhesive holds the at least one leg of the housing in the at least one anchoring portion of the at least one lumen.

8. The medical device of claim 1, wherein the base further comprises a conical concave surface for aligning the endoscopic device with the hole as the endoscopic device is deployed.

9. The medical device of claim 8, wherein the endoscopic device further comprises a hub sized to interfere with the conical concave surface and prevent the endoscopic device from exiting the distal end of the at least one lumen.

10. The medical device of claim 1, wherein the at least one leg further comprises an inner surface that defines a travel path of the endoscopic device and prevents the endoscopic device from puncturing the member.

11. The medical device of claim 1, wherein a outer surface of the housing comprises a non-conductive material.

12. The medical device of claim 1, wherein the endoscopic device is a needle and the actuator is a tube.

13. A medical device for performing endoscopic procedures, comprising:

a member having a first lumen and a second lumen, each lumen having a proximal end and a distal end, wherein the first lumen has both a device portion and at least one anchoring portion, wherein the device portion is defined by at least one curved walled, wherein the device portion and the at least one anchoring portion are disposed parallel along a length of the member;

a first actuator and a second actuator, each actuator having a proximal end and a distal end, wherein the first actuator is disposed within the device portion of the first lumen and the second actuator is disposed within the second lumen;

a first endoscopic device and a second endoscopic device, wherein the first endoscopic device is attached to the distal end of the first actuator and the second endoscopic device is attached to the distal end of the second actuator; and a housing having a base and at least one leg, wherein the at least one leg is fixed to the at least one anchoring portion at a location radially beyond the curved wall portion relative to a centerpoint of the device portion, and the base has a hole sized to permit deployment of the first endoscopic device therethrough.

14. The medical device of claim 13, wherein the first endoscopic device includes a needle and the second endoscopic device includes a snare.

15. A medical device for performing endoscopic procedures, comprising:

a member having a lumen extending from a proximal end to a distal end, wherein the lumen has a device portion, a first anchoring portion, and a second anchoring portion disposed remotely from the first anchoring portion, wherein the device portion, the first anchoring portion and the second anchoring portion are disposed parallel along a length of the member, and the device portion is defined by two walled portions defining an inner channel;

an actuator tube having a proximal end and a distal end, the tube disposed within the device portion of the lumen;

a needle attached to the distal end of the actuator tube; and a housing having a base, a first leg, and a second leg, wherein the first leg is fixed relative to the first anchoring portion and the second leg is fixed relative to the second anchoring portion, wherein the base has a hole sized to permit deployment of the needle and a conical concave surface for aligning the needle with the hole as the needle is deployed, and the first leg and the second leg are disposed radially beyond the inner channel defined by the two walled portions relative to a centerpoint of the device portion.

16. The medical device of claim 15, wherein the first leg and the second leg each comprise an inner surface, wherein the inner surface of the first leg and the inner surface of the second leg form a partial-walled cylinder defining a travel path of the needle and actuator tube.

17. A medical device for performing endoscopic procedures, comprising:

a catheter having a first lumen and a second lumen, each lumen having a proximal end and a distal end, wherein the first lumen defines three contiguous and parallel portions including a device portion, a first anchoring portion, and a second anchoring portion disposed remotely from the first anchoring portion, wherein the device portion is defined by two opposing curved walled portions partially defining a cylinder;

an actuator tube having a proximal end and a distal end disposed within the device portion of the first lumen;

a cable having a proximal end and a distal end disposed within the second lumen;

a needle attached to the distal end of the actuator tube;

a snare assembly attached to the distal end of the cable; and a needle housing having a base, a first leg extending from the base, and a second leg extending from the base, wherein the first leg is fixed within a distal end of the first anchoring portion and the second leg is fixed within a distal end of the second anchoring portion, wherein the base has a hole sized to permit deployment of the needle therethrough and a conical concave surface on a proximal side thereof, and the first leg and the second leg are each disposed entirely outside of the cylinder partially defined by the two curved walled portions.

* * * * *

UNITED STATES PATENT AND TRADEMARK OFFICE
CERTIFICATE OF CORRECTION

PATENT NO. : 8,343,168 B2
APPLICATION NO. : 12/021903
DATED : January 1, 2013
INVENTOR(S) : Christopher J. Kaye et al.

It is certified that error appears in the above-identified patent and that said Letters Patent is hereby corrected as shown below:

On title page, item 75 Inventors,
replace "Christopher J. Kaye, Concord, OH (US); K. Randall John, Chardon, OH; Alexis Uspenski, Rock Creek,OH (US)"
with "Christopher J. Kaye, Concord, OH (US); K. Randall John, Chardon, OH; Alexis Uspenski, Rock Creek, OH (US); Cynthia A. Ranallo, Eastlake, OH (US)"

Signed and Sealed this
Twelfth Day of April, 2016

Michelle K. Lee
*Director of the United States Patent and Trademark Office*